(12) United States Patent
McInally et al.

(10) Patent No.: US 7,605,159 B2
(45) Date of Patent: Oct. 20, 2009

(54) CATHEPSIN CYSTEINE PROTEASE INHIBITORS AND THEIR USE

(75) Inventors: Judith McInally, Loughborough (GB); Garry Pairaudeau, Loughborough (GB); Anil Patel, Loughborough (GB); Stephen Thom, Loughborough (GB)

(73) Assignee: AstraZeneca AB (SE)

( * ) Notice: Subject to any disclaimer, the term of this patent is extended or adjusted under 35 U.S.C. 154(b) by 434 days.

(21) Appl. No.: 10/538,452

(22) PCT Filed: Dec. 11, 2003

(86) PCT No.: PCT/SE03/01931

§ 371 (c)(1),
(2), (4) Date: Jun. 10, 2005

(87) PCT Pub. No.: WO2004/054987

PCT Pub. Date: Jul. 1, 2004

(65) Prior Publication Data

US 2006/0111364 A1 May 25, 2006

(30) Foreign Application Priority Data

Dec. 13, 2002 (SE) .................................. 0203712

(51) Int. Cl.
*A61K 31/535* (2006.01)
*C07D 413/12* (2006.01)

(52) U.S. Cl. ................................... 514/235.8; 544/122

(58) Field of Classification Search ................ 544/122; 514/235.8
See application file for complete search history.

(56) References Cited

FOREIGN PATENT DOCUMENTS

| WO | WO01/09110 | 2/2001 |
|----|------------|--------|
| WO | WO01/49288 | 7/2001 |
| WO | WO 01/68645 | 9/2001 |
| WO | WO 02/069901 | 9/2002 |
| WO | WO03/048123 | 6/2003 |
| WO | WO2004/056324 | 7/2004 |

OTHER PUBLICATIONS

Leroy et al., Expert Opinion on Therapeutic Patents, vol. 14(3), pp. 301-311, (2004).*
Vasiljeva et al., Current Pharmaceutical Design, vol. 13, pp. 387-403 (2007).*
Palermo et al., Trends in Pharmacological Sciences, vol. 29, No. 1, pp. 22-28, (2007).*
Cai et al. "Cathepsin K Inhibitors 2000-2004" Expert Opinion Ther. Patents. 2005 (15) 33-48.

* cited by examiner

*Primary Examiner*—Rebecca L Anderson
(74) *Attorney, Agent, or Firm*—Fish & Richardson P.C.

(57) ABSTRACT

The present invention relates to compounds and compositions for treating diseases associated with cysteine protease activity. The compounds are reversible inhibitors of cysteine proteases S, K, F, L and B. Of particular interest are diseases associated with Cathepsin S. In addition this invention also discloses processes for the preparation of such inhibitors.

15 Claims, No Drawings

CATHEPSIN CYSTEINE PROTEASE INHIBITORS AND THEIR USE

CROSS-REFERENCE TO RELATED APPLICATIONS

This application is the National Stage of International Application No. PCT/SE2003/001931, filed Dec. 11, 2003, which claims the benefit of Swedish Patent Application Serial No. 0203712-5, filed Dec. 13, 2002. The contents of both applications are hereby incorporated by reference in their entireties.

The present invention relates to compounds and compositions for treating diseases associated with cysteine protease activity. The compounds are reversible inhibitors of cysteine proteases S, K, F, L and B. Of particular interest are diseases associated with Cathepsin S. In addition this invention also discloses processes for the preparation of such inhibitors.

BACKGROUND OF THE INVENTION

Cathepsin S is a member of the papain superfamily of cysteine proteases which also encompasses Cathepsins B, H, L, O and K. Cathepsin S plays a key role in the processing of invariant chain in MHC class II complexes allowing the complex to associate with antigenic peptides. MHC class II complexes are then transported to the surface of the cell for presentation to effector cells such as T cells. The process of antigen presentation is a fundamental step in initiation of the immune response. In this respect inhibitors of cathepsin S could be useful agents in the treatment of inflammation and immune disorders such as, but not limited to, asthma, rheumatoid arthritis, multiple sclerosis and Crohn's disease. Cathepsin S has also been implicated in a variety of other diseases involving extracellular proteolysis such as the development of emphysema in COPD through degradation of elastin and in Alzheimers disease.

Other Cathepsins notably K and L have been shown to degrade bone collagen and other bone matrix proteins. Inhibitors of these cysteine proteases would be expected to be useful in the treatment of diseases involving bone resorption such as osteoporosis.

The present invention therefore provides a compound of formula (I)

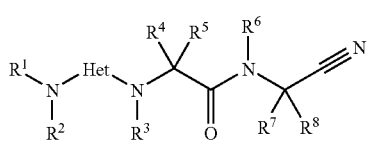

(I)

$R^1$ is independently hydrogen, $C_{1-6}$alkyl or $C_{3-6}$ cycloalkyl $R^2$ is independently aryl, heteroaryl or a group $C_{1-6}$alkyl$R^9$, $CO(C_{1-6}alkyl)R^9$ or $SO_2(C_{1-6}alkyl)R^9$; where $R^9$ is aryl or heteroaryl or $R^1$ and $R^2$ together with the nitrogen atom to which they are attached form a 4 to 7-membered saturated ring optionally containing a carbonyl group, O, S or N atom and optionally substituted by one or more $C_{1-6}$alkyl, amino, hydroxy, $CO_2C_{1-6}$alkyl, $COC_{1-6}$alkyl, halogen, $C_{1-6}$alkylhydroxy, $NR^{10}R^{11}$ where $R^{10}$ and $R^{11}$ are independently hydrogen, $C_{1-6}$alkyl or together with the nitrogen atom to which they are attached form a 5- or 6-membered saturated ring optionally containing a further O, S or $NR^1$ group, $C_{1-6}$alkyl$NR^{12}R^{13}$ where $R^{12}$ and $R^{13}$ are independently hydrogen or $C_{1-6}$alkyl, $CONR^{12}R^{13}$, or optionally substituted by $C_{1-6}$alkyl$R^9$, aryl, phenoxy, COaryl, COheteroaryl or a heteroaryl group, the latter six groups being optionally substituted by halogen, amino, hydroxy, cyano, nitro, carboxy, $CONR^{12}R^{13}$, $SO_2NR^{12}R^{13}$, $SO_2R^{12}$, trifluoromethyl, $NHSO_2R^{12}$, $NHCOR^{12}$, ethylenedioxy, methylenedioxy, $C_{1-6}$alkyl, $C_{1-6}$alkoxy, $C_{1-6}$ alkyl $NR^{10}R^{11}$, $SR^{12}$ or $NR^{10}R^{11}$;

Het is a heteroaryl ring chosen from pyridine, pyrimidine, pyrazine, pyridazine or triazine and optionally substituted by halogen, amino, hydroxy, cyano, nitro, carboxy, $CONR^{12}R^{13}$, $SO_2NR^{12}R^{13}$, $SO_2R^{12}$, trifluoromethyl, $NHSO_2R^{12}$, $NHCOR^{12}$, $C_{1-6}$alkyl, $C_{1-6}$alkoxy, $SR^{12}$ or $NR^{10}R^{11}$;

$R^3$ is independently hydrogen, $C_{1-6}$alkyl or $C_{3-6}$cycloalkyl;

$R^4$ is independently hydrogen, $C_{1-8}$alkyl, $C_{3-8}$cycloalkyl, aryl$C_{1-5}$alkyl or heteroaryl$C_{1-5}$alkyl, the latter three groups being optionally substituted by one or more halogen, amino, hydroxy, $C_{1-6}$alkyl, $C_{1-6}$alkoxy, $SR^{12}$ or $NR^{10}R^{11}$;

$R^5$ is independently hydrogen, $C_{1-6}$alkyl or $C_{3-6}$cycloalkyl;

$R^6$ is independently hydrogen, $C_{1-6}$alkyl or $C_{3-6}$cycloalkyl;

$R^7$ is independently hydrogen, $C_{1-6}$alkyl or $C_{3-6}$cycloalkyl;

$R^8$ is independently hydrogen, aryl, heteroaryl or $C_{1-6}$alkyl optionally substituted with one or more aryl, heteroaryl, halogen, amino, hydroxy, carboxy, $CONR^{12}R^{13}$, $SO_2NR^{12}R^{13}$, $SO_2R^{12}$, $NHSO_2R^{12}$, $NHCOR^{12}$, $C_{1-6}$alkyl, $C_{3-6}$cycloalkyl, $C_{1-6}$alkoxy, $SR^{12}$ or $NR^{10}R^{11}$;

or a pharmaceutically acceptable salt thereof.

Aryl groups include phenyl and naphthyl. Heteroaryl groups include 5- or 6-membered, 5,6- or 6,6-fused heterocyclic rings containing one or more heteroatoms selected from N, S or O. Examples include pyridinyl, pyrimidinyl, thiazolyl, oxazolyl, pyrazole, imidazolyl, furyl, thienyl, quinolinyl, isoquinolinyl, benzimidazolyl, benzofuryl, benzothienyl and indolyl.

Aryl and heteroaryl groups can be optionally substituted by on or more of the following groups; halogen, amino, hydroxy, cyano, nitro, carboxy, $CONR^{12}R^{13}$, $SO_2NR^{12}R^{13}$, $SO_2R^{12}$, trifluoromethyl, $NHSO_2R^{12}$, $NHCOR^{12}$, ethylenedioxy, methylenedioxy, $C_{1-6}$alkyl, $C_{1-6}$alkoxy, $C_{1-6}$alkyl $NR^{10}R^{11}$, $SR^{12}$ or $NR^{10}R^{11}$.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Preferably $R^1$ is hydrogen or $C_{1-6}$alkyl, more preferably methyl and $R^2$ is $CH_2R^9$ or $CH_2CH_2R^9$ where $R^9$ is phenyl or a 5- or 6-membered aromatic ring containing one or two heteroatoms and optionally substituted by $C_{1-6}$alkyl. More preferably $R^2$ is $CH_2R^9$ or $CH_2CH_2R^9$ where $R^9$ is phenyl, pyridyl or oxazole substituted by methyl.

Alternatively $R^1$ and $R^2$ form a piperidine, piperazine, pyrrolidine, morpholine, or thiomorpholine ring optionally substituted by $CH_2OH$, $CH_2CH_2OH$, hydroxy, $CONH_2$, phenyl, phenoxy, C(O)-furyl, the latter three groups being optionally substituted by halogen, in particular chloro.

Preferably Het is pyrimidine ring.
Preferably $R^3$ is hydrogen.
Preferably $R^4$ is hydrogen.
Preferably $R^5$ is $C_{1-6}$alkyl, more preferably iso-butyl.
Preferably $R^6$ is hydrogen.
Preferably $R^7$ and $R^8$ are both hydrogen.

Preferred compounds of the invention include:

N~1~-[Cyano(2-methoxyphenyl)methyl]-N~2~-(2-morpholin-4-ylpyrimidin-4-yl)-L-leucinamide N~1~-[Cyano(2-methoxyphenyl)methyl]-N~2~-(2-piperazin-1-ylpyrimidin-4-yl)-L-leucinamide, N-[Cyano(2-methoxyphenyl)methyl]-N-(2-morpholin-4-ylpyrimidin-4-yl)-L-phenylalaninamide N~1~-[Cyano(2-methoxyphenyl)methyl]-3-cyclohexyl-N~2~-(2-morpholin-4-ylpyrimidin-4-yl)-L-alaninamide N-[2-(Benzylamino)pyrimidin-4-yl]-N-(cyanomethyl)-L-phenylalaninamide N-{2-[Benzyl(methyl)amino]pyrimidin-4-yl}-N-(cyanomethyl)-L-phenylalaninamide N-{2-[4-(4-Chlorophenyl)piperazin-1-yl]pyrimidin-4-yl}-N-(cyanomethyl)-L-phenylalaninamide N~2~-[2-(Benzylamino)pyrimidin-4-yl]-N~1~-(cyanomethyl)-3-cyclohexyl-L-alaninamide N~2~-{2-[Benzyl(methyl)amino]pyrimidin-4-yl}-N~1~-(cyanomethyl)-3-cyclohexyl-L-alaninamide N~2~-{2-[4-(4-Chlorophenyl)piperazin-1-yl]pyrimidin-4-yl}-N~1~-(cyanomethyl)-3-cyclohexyl-L-alaninamide N~1~-(Cyanomethyl)-N~2~-(4-morpholin-4-ylpyrimidin-2-yl)-L-leucinamide N~1~-(Cyanomethyl)-N~2~-(2-morpholin-4-ylpyrimidin-4-yl)-L-leucinamide N~1~-(Cyanomethyl)-N~2~-[2-(4-hydroxy-4-phenylpiperidin-1-yl)pyrimidin-4-yl]-L-leucinamide N~1~-(Cyanomethyl)-N~2~-{2-[methyl(pyridin-3-ylmethyl)amino]pyrimidin-4-yl}-L-leucinamide N~2~-{2-[Benzyl(methyl)amino]pyrimidin-4-yl}-N~1~-(cyanomethyl)-L-leucinamide N~2~-{2-[4-(4-Chlorophenyl)piperazin-1-yl]pyrimidin-4-yl}-N~1~-(cyanomethyl)-L-leucinamide, N~2~-{2-[4-(5-Chloropyridin-2-yl)piperazin-1-yl]pyrimidin-4-yl}-N~1~-(cyanomethyl)-L-leucinamide, N~1~-(Cyanomethyl)-N~2~-{2-[methyl(thien-3-ylmethyl)amino]pyrimidin-4-yl}-L-leucinamide N~1~-(Cyanomethyl)-N~2~-(2-thiomorpholin-4-ylpyrimidin-4-yl)-L-leucinamide N~1~-(Cyanomethyl)-N~2~-[2-(4-phenylpiperazin-1-yl)pyrimidin-4-yl]-L-leucinamide N~1~-(Cyanomethyl)-N~2~-{2-[2-(hydroxymethyl)piperidin-1-yl]pyrimidin-4-yl}-L-leucinamide N~1~-(Cyanomethyl)-N~2~-{2-[(2R)-2-(hydroxymethyl)pyrrolidin-1-yl]pyrimidin-4-yl}-L-leucinamide N~1~-(Cyanomethyl)-N~2~-[2-(4-hydroxypiperidin-1-yl)pyrimidin-4-yl]-L-leucinamide N~1~-(Cyanomethyl)-N~2~-{2-[4-(2-furoyl)piperazin-1-yl]pyrimidin-4-yl}-L-leucinamide, N~1~-(Cyanomethyl)-N~2~-{2-[methyl(2-pyridin-2-ylethyl)amino]pyrimidin-4-yl}-L-leucinamide N~2~-[2-(4-Benzylpiperidin-1-yl)pyrimidin-4-yl]-N~1~-(cyanomethyl)-L-leucinamide N~1~-(Cyanomethyl)-N~2~-[2-(4-pyridin-2-ylpiperazin-1-yl)pyrimidin-4-yl]-L-leucinamide N~1~-(Cyanomethyl)-N~2~-[2-(4-phenylpiperidin-1-yl)pyrimidin-4-yl]-L-leucinamide N~1~-(Cyanomethyl)-N~2~-{2-[4-(2-hydroxyethyl)piperidin-1-yl]pyrimidin-4-yl}-L-leucinamide N~2~-{2-[4-(3-Chlorophenyl)piperazin-1-yl]pyrimidin-4-yl}-N~1~-(cyanomethyl)-L-leucinamide N~1~-(Cyanomethyl)-N~2~-[2-(4-phenoxypiperidin-1-yl)pyrimidin-4-yl]-L-leucinamide N~1~-(Cyanomethyl)-N~2~-[2-(3-phenylpyrrolidin-1-yl)pyrimidin-4-yl]-L-leucinamide N~1~-(Cyanomethyl)-N~2~-(2-{methyl[(3-methylisoxazol-5-yl)methyl]amino}pyrimidin-4-yl)-L-leucinamide and pharmaceutically acceptable salts thereof.

The present invention further provides a process for the preparation of a compound of formula (I) which comprises
(i) reaction of a compound of general formula (II)

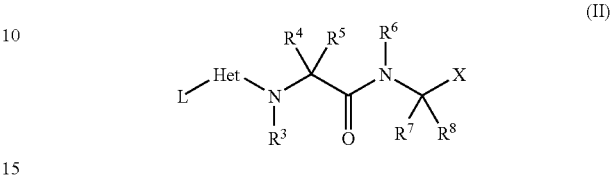

wherein L represents a leaving group (e.g. halide, sulphide, sulfoxide or sulphone group), preferably the sulphide is oxidised to a sulphoxide or sulphone group before displacement. An oxidising agent such as a peracid may be used, for example meta-chloroperbenzoic acid in dichloromethane at room temperature.

L may be displaced by $NR^1R^2$ respectively where $R^1$ and $R^2$ are defined in formula (I). The reaction may be performed in an inert solvent for example dioxane, N,N-dimethylformamide at ambient temperature or with heating, usually with a base present for example N,N-diisopropylethylamine.

X may be CN, or a group that can be readily converted into a nitrile, for example C1-6alkoxycarbonyl, $CONH_2$ or $CO_2H$.

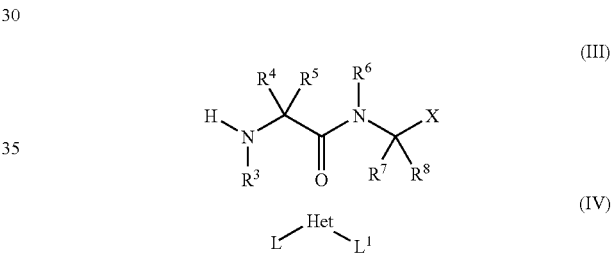

Compounds of formula (II) may be prepared from compounds of formula (III) by displacement of a leaving group $L^1$ from compounds of formula (IV).

Wherein $L^1$ represents a leaving group (e.g. halide, sulphide, sulfoxide or sulphone group), preferably the sulphide is oxidised to a sulphoxide or sulphone group before displacement. An oxidising agent such as a peracid may be used, for example meta-chloroperbenzoic acid in dichloromethane at room temperature. The reaction may be performed in an inert solvent for example dioxane, N,N-dimethylformamide at ambient temperature or with heating, usually with a base present for example N,N-diisopropylethylamine.

Compounds of formula (III) may be prepared from the reaction of compounds of formula (V) with compounds of formula (VI) using an appropriate coupling agent, for example N-(3-dimethylaminopropyl)-N'-ethylcarbodiimide, carbonyl diimidazole. Alternatively the acid may be activated by formation of the acid chloride using for example, oxalyl chloride.

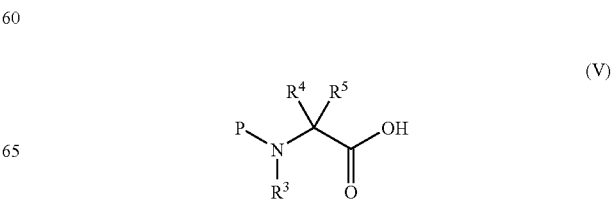

-continued

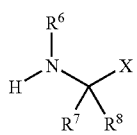
(VI)

P is a nitrogen protecting group for example tert-butylcarbamate, benzyl carbamate, benzyl.

Compound of general formula (II) may also be prepared from the reaction of compounds of formula (VII) with compounds of formula (VI) using an appropriate coupling agent, for example N-(3-dimethylaminopropyl)-N'-ethylcarbodiimide, carbonyl diimidazole. Alternatively the acid may be activated by formation of the acid chloride using for example, oxalyl chloride.

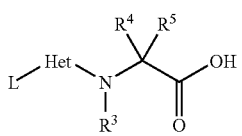
(VII)

(ii) reaction of a compound of general formula (VII) with compounds of formula (III) or reaction of a compound of general formula (IX) with a compound of general formula (VI).

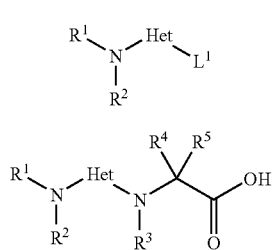
(VIII)

(IX)

According to a further feature of the invention there is provided a compound of the formula (I), or a pharmaceutically acceptable salt thereof, for use as a therapeutic agent.

According to a further feature of the present invention there is provided a method for producing inhibition of a cysteine protease in a warm blooded animal, such as man, in need of such treatment, which comprises administering to said animal an effective amount of a compound of the present invention, or a pharmaceutically acceptable salt thereof. In particular the compounds of the invention are useful in the treatment of inflammation and immune disorders such as, but not limited to, asthma, rheumatoid arthritis, COPD, multiple sclerosis, Crohn's disease, Alzheimers and pain, such as neuropathic pain. Preferably the compounds of the invention are used to treat pain, especially neuropathic pain.

The invention also provides a compound of the formula (I), or a pharmaceutically acceptable salt thereof, for use as a medicament; and the use of a compound of the formula (I) of the present invention, or a pharmaceutically acceptable salt thereof, in the manufacture of a medicament for use in the inhibition of a cysteine protease in a warm blooded animal, such as man.

In particular the invention provides the use of a compound of the formula (I) of the present invention, or a pharmaceutically acceptable salt thereof, in the manufacture of a medicament for use in the inhibition of Cathepsin S in a warm blooded animal, such as man. In order to use a compound of the formula (I) or a pharmaceutically acceptable salt thereof for the therapeutic treatment of mammals including humans, in particular in the inhibition of a cysteine protease, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt thereof and a pharmaceutically acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, an intravenous, subcutaneous or intramuscular dose of 1 mgkg$^{-1}$ to 100 mgkg$^{-1}$ of the compound, preferably in the range of 5 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I), or a pharmaceutically-acceptable salt thereof (hereafter compound X), for therapeutic or prophylactic use in humans:

| (a) | |
| --- | --- |
| Tablet I | mg/tablet |
| Compound X. | 100 |
| Lactose Ph.Eur. | 179 |
| Croscarmellose sodium | 12.0 |
| Polyvinylpyrrolidone | 6 |
| Magnesium stearate | 3.0 |

| (b) | |
| --- | --- |
| Tablet II | mg/tablet |
| Compound X | 50 |
| Lactose Ph.Eur. | 229 |
| Croscarmellose sodium | 12.0 |
| Polyvinylpyrrolidone | 6 |
| Magnesium stearate | 3.0 |

-continued

(c)

| Tablet III | mg/tablet |
|---|---|
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph.Eur. | 389 |
| Croscarmellose sodium | 100 |
| Magnesium stearate | 1. |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β cyclodextrin may be used to aid formulation.

Note

The above formulations may be obtained by conventional procedures well known in the pharmaceutical art. The tablets (a)-(c) may be enteric coated by conventional means, for example to provide a coating of cellulose acetate phthalate.

The following examples illustrate the invention.

EXAMPLE 1

N~1~-[Cyano(2-methoxyphenyl)methyl]-N~2~-(2-morpholin-4-ylpyrimidin-4-yl)-L-leucinamide (i) N~2~-(tert-Butoxycarbonyl)-N~1~-[cyano(2-methoxyphenyl)methyl]-L-leucinamide 1-(3-Dimethylaminopropyl)-3-ethylcarbodiimide hydrochloride (2.9 g) and 1-hydroxybenzotriazole hydrate (2.0 g) were added to a solution of 2-methoxyphenylamino acetonitrile (2.0 g) and N-tert-butoxycarbonyl L-leucine (2.5 g) in N,N-dimethylformamide (20 ml) at room temperature followed by N,N-diisopropylethylamine (5.3 ml) and stirred at room temperature overnight. The mixture was diluted with water, extracted into ethyl acetate and dried (MgSO$_4$). The solvent was removed under vacuum to leave an oil which was subjected to column chromatography on silica eluting with isohexane/ethyl acetate 2:1 to give a colourless oil (3.7 g).

MS: APCI(+ve) 249 (M-Boc-CN+1)

(ii) N~1~-[Cyano(2-methoxyphenyl)methyl]-L-leucinamide

The product from step (i) (3.70 g) in formic acid (40 ml) was stirred for 90 min at room temperature then the solvent was removed under vacuum to give a yellow oil (2.7 g).

MS: APCI(+ve) 276 (M-Boc+1)

(iii) N~1~-[Cyano(2-methoxyphenyl)methyl]-N~2~-(2-fluoropyrimidin-4-yl)-L-leucinamide A solution of the product from step (ii) (2.7 g) and N,N-diisopropylethylamine (1.7 ml) in tetrahydrofuran (40 ml) was added dropwise to a solution of 2,4-difluoropyrimidine (1.15 g) in tetrahydrofuran (40 ml) and N,N-diisopropylethylamine (1.7 ml). After stirring at room temperature overnight the solvent was removed under vacuum to yield a crude oil which was subjected to column chromatography on silica eluting with dichloromethane/ethyl acetate 2:1 to give a colourless oil (1.50 g).

MS: APCI(+ve) 372 (M+1)

(iv) N~1~-[Cyano(2-methoxyphenyl)methyl]-N~2~-(2-morpholin-4-ylpyrimidin-4-yl)-L-leucinamide The product from step (iii) (0.5 g), morpholine (0.12 ml) and N,N-diisopropylethylamine (0.24 ml) in tetrahydrofuran (20 ml) was stirred at room temperature overnight. The solvent was removed under vacuum to yield a crude oil which was subjected to column chromatography on silica eluting with ethyl acetate/isohexane 3:1 to give a white solid (0.4 g).

MS: APCI(+ve) 439 (M+1)

1H NMR: δ (DMSO) 9.40 (1H, m), 9.08 (1H, m), 7.78-7.12 (5H, m), 6.10-6.08 (1H, d), 5.80 (1H, m), 4.60-4.40 (1H, m), 3.84-3.51 (11H, m), 1.80-1.20 (3H, m), 0.96-0.84 (6H, m).

EXAMPLE 2

N~1~-[Cyano(2-methoxyphenyl)methyl]-N~2~-(2-piperazin-1-ylpyrimidin-4-yl)-L-leucinamide, Trifluoroacetate Salt The title compound was prepared according to the procedure in example 1 step (iv) using piperazine.

MS: APCI(+ve) 438 (M+1)

1H NMR: δ (DMSO) 8.83-8.81 (2H, m), 7.79-6.97 (5H, m), 6.09-6.02 (2H, m), 4.40 (1H, m), 3.85 (7H, bm), 3.13-3.05 (4H, m), 1.68-1.49 (3H, m), 0.94-0.84 (6H, m).

EXAMPLE 3

N-[Cyano(2-methoxyphenyl)methyl]-N-(2-morpholin-4-ylpyrimidin-4-yl)-L-phenylalaninamide (i) N-(tert-Butoxycarbonyl)-N-[cyano(2-methoxyphenyl)methyl]-L-phenylalaninamide The sub-title compound was prepared from N-butoxycarbonyl-L-phenylalanine (1.32 g) by the method of example 1 step (i). Yield 2.05 g.

MS: APCI(+ve) 310 (M-Boc+1)

(ii) N-[Cyano(2-methoxyphenyl)methyl]-N-(2-fluoropyrimidin-4-yl)-L-phenylalaninamide The sub-title compound was prepared from the product of step (i) (2.05 g) by the method of example 1 steps (ii) and (iii). Yield 0.57 g.

MS: APCI(+ve) 406 (M+1)

(iii) N-[Cyano(2-methoxyphenyl)methyl]-N-(2-morpholin-4-ylpyrimidin-4-yl)-L-phenylalaninamide The title compound was prepared from the product of step (ii) (0.25 g) by the method of example 1 step (iv). Yield 0.078 g.

MS: APCI(+ve) 473 (M+1)

NMR: δ (DMSO) 9.29 and 9.15 (1H, 2×d), 7.73 and 7.69 (1H, 2×d), 7.45-7.40 (2H, m), 7.33-7.17 (6H, m), 7.11 (1H, m), 7.00 (1H, m), 6.08 (1H, dd), 5.88 and 5.85 (1H, 2×d), 4.64 (1H, brs), 3.83 and 3.80 (3H, 2×s), 3.58 (4H, m), 3.47 (4H, m), 3.05-2.82 (2H, m).

EXAMPLE 4

N~1~-[Cyano(2-methoxyphenyl)methyl]-3-cyclohexyl-N~2~-(2-morpholin-4-ylpyrimidin-4-yl)-L-alaninamide (i) N-(tert-Butoxycarbonyl)-N-[cyano(2-methoxyphenyl)methyl]-3-cyclohexyl-L-alaninamide The sub-title compound was prepared from N-butoxycarbonyl-beta-cyclohexyl-L-alanine (1.36 g) by the method of example 1 step (i). Yield 1.99 g. Used directly in the next step.

(ii) N~1~-[Cyano(2-methoxyphenyl)methyl]-3-cyclohexyl-N~2~-(2-fluoropyrimidin-4-yl)-L-alaninamide The sub-title compound was prepared from the product of step (i) (1.99 g) by the method of example 1 steps (ii) and (iii). Yield 0.12 g.

MS: APCI(+ve) 412 (M+1)

(iii) N~1~-[Cyano(2-methoxyphenyl)methyl]-3-cyclohexyl-N~2~-(2-morpholin-4-ylpyrimidin-4-yl)-L-alaninamide The title compound was prepared from the product of step (ii) (0.12 g) by the method of example 1 step (iv). Yield 0.087 g.

MS: APCI(+ve) 479 (M+1)

NMR: δ (DMSO) 9.18 and 9.06 (1H, 2×d), 7.76 and 7.72 (1H, 2×d), 7.49-7.37 (2H, m), 7.24 (1H, brs), 7.11 (1H, d), 7.02 (1H, t), 6.09 (1H, m), 5.91 and 5.88 (1H, 2×d), 4.46 and 4.36 (1H, 2×brs), 3.82 and 3.80 (3H, 2×s), 3.60 (4H, m), 3.47 (4H, m), 1.76-1.36 (8H, m), 1.24-1.09 (3H, m), 0.98-0.83 (2H, m).

EXAMPLE 5

N-[2-(Benzylamino)pyrimidin-4-yl]-N-(cyanomethyl)-L-phenylalaninamide (i) N-(tert-Butoxycarbonyl)-N-(cyanomethyl)-L-phenylalaninamide The sub-title compound was prepared from aminoacetonitrile hydrochloride by the method of example 1 step (i).

MS: APCI(+ve) 204 (M-Boc+1)

(ii) N-(Cyanomethyl)-N-(2-fluoropyrimidin-4-yl)-L-phenylalaninamide

The sub-title compound was prepared from the product of step (i) (3.5 g) by the method of example 1 steps (ii) and (iii). Yield 1.11 g.

MS: APCI(+ve) 300 (M+1)

(iii) N-[2-(Benzylamino)pyrimidin-4-yl]-N-(cyanomethyl)-L-phenylalaninamide

The title compound was prepared from the product from step (ii) (0.2 g) and benzylamine (0.37 ml) by the method of example 1 step (iv). Yield 0.11 g.

MS: APCI(+ve) 387 (M+1)

NMR: δ (DMSO) 8.60 (1H, brs), 7.61 (1H, d), 7.29-7.14 (10H, m), 6.93 (1H, brs), 5.78 (1H, d), 4.64 (1H, brs), 4.47-4.33 (2H, m), 4.05 (2H, brs), 3.03 (1H, dd), 2.85 (1H, m).

EXAMPLE 6

N-{2-[Benzyl(methyl)amino]pyrimidin-4-yl}-N-(cyanomethyl)-L-phenylalaninamide

The title compound was prepared from the product of example 5 step (ii) (0.2 g) and N-benzylmethylamine by the method of example 1 step (iv). Yield 0.18 g.

MS: APCI(+ve) 401 (M+1)

NMR: δ (DMSO) 8.69 (1H, brs), 7.71 (1H, d), 7.33-7.15 (10H, m), 5.84 (1H, d), 4.75 (2H, q), 4.62 (1H, brs), 4.03 (2H, brs), 2.99 (1H, dd), 2.94 (3H, s), 2.86 (1H, m).

EXAMPLE 7

N-{2-[4-(4-Chlorophenyl)piperazin-1-yl]pyrimidin-4-yl}-N-(cyanomethyl)-L-phenylalaninamide The title compound was prepared from the product of example 5 step (ii) (0.2 g) and 4(4-chlorophenyl)piperazine by the method of example 1 step (iv). Yield 0.18 g.

MS: APCI(+ve) 476 (M+1)

NMR: δ (DMSO) 8.77 (1H, t), 7.72 (1H, d), 7.40 (1H, brs), 7.31-7.17 (7H, m), 6.98 (2H, d), 5.86 (1H, d), 4.54 (1H, brs), 4.13 (2H, m), 3.74 (4H, m), 3.12 (4H, m), 3.01 (1H, dd), 2.89 (1H, m).

EXAMPLE 8

N~2~-[2-(Benzylamino)pyrimidin-4-yl]-N~1~-(cyanomethyl)-3-cyclohexyl-L-alaninamide (i) N-(tert-butoxycarbonyl)-N-(cyanomethyl)-3-cyclohexyl-L-alaninamide The sub-title compound was prepared from N-butoxycarbonyl-beta-cyclohexyl-L-alanine (5.0 g) and aminoacetonitrile hydrochloride (1.71 g) by the method of example 1 step (i). Yield 4.09 g.

MS: APCI(+ve) 210 (M-Boc+H)

(ii) N~1~-(Cyanomethyl)-3-cyclohexyl-N~2~-(2-fluoropyrimidin-4-yl)-L-alaninamide The sub-title compound was prepared from the product of step (i) (4.09 g) by the method of example 1 steps (ii) and (iii). Yield 1.00 g.

MS: APCI(+ve) 306 (M+1)

(iii) N~2~-[2-(Benzylamino)pyrimidin-4-yl]-N~1~-(cyanomethyl)-3-cyclohexyl-L-alaninamide The title compound was prepared from the product of step (ii) (0.2 g) by the method of example 1 step (iv). Yield 0.05 g.
MS: APCI(+ve) 393 (M+1)
NMR: δ (DMSO) 8.48 (1H, brs), 7.64 (1H, d), 7.31-7.24 (4H, m), 7.17 (1H, m), 7.09 (1H, brs), 6.93 (1H, brs), 5.81 (1H, d), 4.47-4.36 (3H, m), 4.04 (2H, d), 1.75-1.47 (7H, m), 1.31 (1H, m), 1.19-1.09 (3H, m), 0.86 (2H, m).

EXAMPLE 9

N~2~-{2-[Benzyl(methyl)amino]pyrimidin-4-yl}-N~1~-(cyanomethyl)-3-cyclohexyl-L-alaninamide The title compound was prepared from the product of example 8 step (ii) (0.2 g) and N-benzylmethylamine (0.43 ml) by the method of example 1 step (iv). Yield 0.13 g.
MS: APCI(+ve) 407 (M+1)
NMR: δ (DMSO) 8.57 (1H, brs), 7.73 (1H, d), 7.31-7.27 (2H, m), 7.23-7.19 (4H, m), 5.85 (1H, d), 4.80 (2H, m), 4.42 (1H, brs), 4.02 (2H, m), 2.95 (3H, s), 1.69-1.44 (7H, m), 1.35 (1H, m), 1.24-1.07 (3H, m), 0.92-0.81 (2H, m).

EXAMPLE 10

N~2~-{2-[4-(4-Chlorophenyl)piperazin-1-yl]pyrimidin-4-yl}-N~1~-(cyanomethyl)-3-cyclohexyl-L-alaninamide The title compound was prepared from the product of example 8 step (ii) (0.2 g) and 4(4-chlorophenyl)piperazine (0.66 g) by the method of example 1 step (iv). Yield 0.2 g.
MS: APCI(+ve) 482 (M+1)
NMR: δ (DMSO) 8.66 (1H, t), 7.75 (1H, d), 7.25 (3H, d), 6.98 (2H, d), 5.89 (1H, d), 4.35 (1H, brs), 4.12 (2H, d), 3.75 (4H, m), 3.13 (4H, m), 1.73-1.46 (7H, m), 1.37 (1H, m), 1.24-1.07 (3H, m), 0.97-0.87 (2H, m).

EXAMPLE 11

N~1~-(Cyanomethyl)-N~2~-(4-morpholin-4-ylpyrimidin-2-yl)-L-leucinamide (i) N~2~-(tert-Butoxycarbonyl)-N~1~-(cyanomethyl)-L-leucinamide The sub-title compound was prepared according to the procedure of example 1 step (i) with amino acetonitrile hydrochloride (2.22 g) and N-tert-butoxy S-leucine (5 g).
MS: APCI(+ve) 270 (M+1)

(ii) N~1~-(Cyanomethyl)-N~2~-(4-fluoropyrimidin-2-yl)-L-leucinamide and N~1~-(Cyanomethyl)-N~2~-(2-fluoropyrimidin-4-yl)-L-leucinamide The sub-title compounds were prepared from the product of step (i) (4.3 g) according to the procedure of example 1 steps (ii) and (iii).

N~1~-(Cyanomethyl)-N~2~-(4-fluoropyrimidin-2-yl)-L-leucinamide

Yield 0.38 g
MS: APCI(+ve) 266 (M+1)

N~1~-(Cyanomethyl)-N~2~-(2-fluoropyrimidin-4-yl)-L-leucinamide

Yield 3.8 g
MS: APCI(+ve) 266 (M+1)

(iii) N~1~-(Cyanomethyl)-N-2~-(4-morpholin-4-ylpyrimidin-2-yl)-L-leucinamide

The title compound was prepared according to the procedure of example 1 step (iv) using N~1~-(cyanomethyl)-N~2~-(4-fluoropyrimidin-2-yl)-L-leucinamide. Yield 0.2 g
MS: APCI(+ve) 333 (M+1)
1H NMR: δ (DMSO) 8.49-8.46 (1H, t), 7.83-7.81 (1H, d), 6.63 (1H, bm), 6.06-6.04 (1H, d), 4.25-4.05 (3H, m), 3.63-3.47 (8H, m), 1.75-1.39 (3H, m), 0.90-0.84 (6H, m).

EXAMPLE 12

N~1~-(Cyanomethyl)-N~2~-(2-morpholin-4-ylpyrimidin-4-yl)-L-leucinamide

The title compound was prepared from N~1~-(cyanomethyl)-N~2~-(2-fluoropyrimidin-4-yl)-L-leucinamide (example 11 step (iii)) according to the procedure of example 1 step (iv). Yield 0.17 g
MS: APCI(+ve) 333 (M+1)
1H NMR: δ (DMSO) 8.64-8.60 (1H, t), 7.74-7.72 (1H, d), 7.24-7.23 (1H, d), 5.89-5.82 (1H, d), 4.31-4.08 (3H, m), 3.58 (8H, m), 1.72-1.39 (3H, m), 0.92-0.84 (6H, m).

Examples 13-34 were prepared according to the procedures of example 1 step (iv) using N~1~-(cyanomethyl)-N~2~-(2-fluoropyrimidin-4-yl)-L-leucinamide (example 11 step (iii)) and the appropriate amine.

EXAMPLE 13

N~1~-(Cyanomethyl)-N~2~-[2-(4-hydroxy-4-phenylpiperidin-1-yl)pyrinidin-4-yl]-L-leucinamide MS: APCI(+ve) 423 (M+1)
1H NMR: δ (DMSO) 8.65-8.61 (1H, t), 7.73-7.14 (7H, m), 5.84-5.82 (1H, d), 5.00-4.39 (4H, m), 4.08-4.03 (2H, m), 3.20-3.12 (2H, m), 1.90-1.35 (7H, m), 0.92-0.85 (6H, m).

EXAMPLE 14

N~1~-(Cyanomethyl)-N~2~-{2-[methyl(pyridin-3-ylmethyl)amino]pyrimidin-4-yl}-L-leucinamide MS: APCI(+ve) 368 (M+1)
1H NMR: δ (DMSO) 8.59-7.20 (7H, m), 5.89-5.87 (1H, d), 4.68 & 4.37 (3H, m), 4.08-4.02 (2H, m), 2.99 (3H, s), 1.68-1.35 (3H, m), 0.93-0.80 (6H, m).

EXAMPLE 15

N~2~-{2-[enzyl(methyl)amino]pyrimidin-4-yl}-N~1~-(cyanomethyl)-L-leucinamide

MS: APCI(+ve) 367 (M+1)
1H NMR: δ (DMSO) 8.57-8.54 (1H, t), 7.74 (1H, d), 7.31-7.18 (6H, m), 5.87-5.85 (1H, d), 4.82-4.00 (5H, m), 2.95 (3H, s), 1.71-1.40 (3H, m), 0.89-0.81 (6H, m).

EXAMPLE 16

N~2~-{2-[4-(4-Chlorophenyl)piperazin-1-yl]pyrimidin-4-yl}-N~1~-(cyanomethyl)-L-leucinamide, Trifluoroacetate Salt MS: APCI(+ve) 442 (M+1)
1H NMR: δ (DMSO) 9.02-9.01 (2H, m), 7.75-6.98 (5H, m), 6.24-6.22 (1H, d), 4.48-4.13 (3H, m), 3.82-3.55 (8H, m), 1.66-1.50 (3H, m), 0.95-0.88 (6H, m).

EXAMPLE 17

N~2~-{2-[4-(5-Chloropyridin-2-yl)piperazin-1-yl]pyrimidin-4-yl}-N~1~-(cyanomethyl)-L-leucinamide, Bis Trifluoroacetate Salt MS: APCI(+ve) 443 (M+1)
1H NMR: δ (DMSO) 9.03-9.01 (2H, m), 8.15-6.90 (4H, m), 6.25-6.23 (1H, d), 4.49 (1H, m), 4.23-4.18 (2H, d), 3.80-3.66 (8H, m), 1.66-1.51 (3H, m), 0.95-0.88 (6H, m).

EXAMPLE 18

N~1~-(Cyanomethyl)-N~2~-{2-[methyl(thien-3-ylmethyl)amino]pyrimidin-4-yl}-L-leucinamide MS: APCI(+ve) 373 (M+1)

EXAMPLE 19

N~1~-(Cyanomethyl)-N~2~-(2-thiomorpholin-4-ylpyrimidin-4-yl)-L-leucinamide

MS: APCI(+ve) 349 (M+1)

EXAMPLE 20

N~1~-(Cyanomethyl)-N~2~-[2-(4-phenylpiperazin-1-yl)pyrimidin-4-yl]-L-leucinamide MS: APCI(+ve) 408 (M+1)

EXAMPLE 21

N~1~-(Cyanomethyl)-N~2~-{2-[2-(hydroxymethyl)piperidin-1-yl]pyrimidin-4-yl}-L-leucinamide MS: APCI(+ve) 361 (M+1)

EXAMPLE 22

N~1~-(Cyanomethyl)-N~2~-{2-[(2R)-2-(hydroxymethyl)pyrrolidin-1-yl]pyrimidin-4-yl}-L-leucinamide MS: APCI(+ve) 347 (M+1)

EXAMPLE 23

N~1~-(Cyanomethyl)-N~2~-[2-(4-hydroxypiperidin-1-yl)pyrimidin-4-yl]-L-leucinamide MS: APCI(+ve) 347 (M+1)

EXAMPLE 24

N~1~-(Cyanomethyl)-N~2~-{2-[4-(2-furoyl)piperazin-1-yl]pyrimidin-4-yl}-L-leucinamide MS: APCI(+ve) 426 (M+1)

EXAMPLE 25

N~2~-{2-[3-(Aminocarbonyl)piperidin-1-yl]pyrimidin-4-yl}-N~1~-(cyanomethyl)-L-leucinamide MS: APCI(+ve) 374 (M+1)

EXAMPLE 26

N~1~-(Cyanomethyl)-N~2~-{2-[methyl(2-pyridin-2-ylethyl)amino]pyridin-4-yl}-L-leucinamide MS: APCI(+ve) 382 (M+1)

EXAMPLE 27

N~2~-[2-(4-Benzylpiperidin-1-yl)pyrimidin-4-yl]-N~1~-(cyanomethyl)-L-leucinamide MS: APCI(+ve) 421 (M+1)

EXAMPLE 28

N~1~-(Cyanomethyl)-N~2~-[2-(4-pyridin-2-ylpiperazin-1-yl)pyrimidin-4-yl]-L-leucinamide MS: APCI(+ve) 409 (M+1)

EXAMPLE 29

N~1~-(Cyanomethyl)-N~2~-[2-(4-phenylpiperidin-1-yl)pyrimidin-4-yl]-L-leucinamide MS: APCI(+ve) 407 (M+1)

EXAMPLE 30

N~1~-(Cyanomethyl)-N~2~-{2-[4-(2-hydroxyethyl)piperidin-1-yl]pyrimidin-4-yl}-L-leucinamide MS: APCI(+ve) 375 (M+1)

EXAMPLE 31

N~2~-{2-[4-(3-Chlorophenyl)piperazin-1-yl]pyrimidin-4-yl}-N~1~-(cyanomethyl)-L-leucinamide MS: APCI(+ve) 442/4 (M+1)

EXAMPLE 32

N~1~-(Cyanomethyl)-N~2~-[2-(4-phenoxypiperidin-1-yl)pyrimidin-4-yl]-L-leucinamide MS: APCI(+ve) 423 (M+1)

EXAMPLE 33

N~1~-(Cyanomethyl)-N~2~-[2-(3-phenylpyrrolidin-1-yl)pyrimidin-4-yl]-L-leucinamide MS: APCI(+ve) 393 (M+1)

EXAMPLE 34

N~1~-(Cyanomethyl)-N~2~-(2-{methyl[(3-methyl-isoxazol-5-yl)methyl]amino}pyrimidin-4-yl)-L-leucinamide MS: APCI(+ve) 372 (M+1)

Measurement of Cathepsin S Activity.

QFRET Technology (Quenched Fluorescent Resonance Energy Transfer) was used to measure the inhibition by test compounds of Cathepsin S-mediated cleavage of the synthetic peptide Z-Val-Val-Arg-AMC. Compounds were screened at five concentrations in duplicate and the $pIC_{50}$ values reported.

Synthetic substrate, 20☐M [final] Z-Val-Val-Arg-AMC in phosphate buffer were added to a 96 well black Optiplate. The assay plates were pre-read for compound auto fluorescence on SpectraMax Gemini at 355 nM excitation and 460 nM emission. 250 pM [final] rHuman Cathepsin S in phosphate buffer was added and incubated for 2 h at room temperature on the SpectraMax Gemini, taking readings every 20 min at 355 nM excitation and 460 nM emission.

Activity Based template (5PTB-8) used the auto fluorescent corrected data to calculate the percentage inhibition for each compound concentration using the relevent plate controls. This data was used to construct inhibition curves and $pIC_{50}$ estimated by non-linear regression using a 4 parameter logistic model.

The invention claimed is:

1. A compound of formula (I):

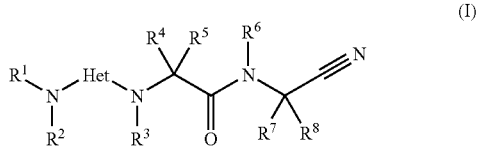

$R^1$ is independently hydrogen, $C_{1-6}$alkyl or $C_{3-6}$cycloalkyl;
$R^2$ is independently aryl, heteroaryl or a group $C_{1-6}$alkyl$R^9$, CO($C_{1-6}$alkyl)$R^9$ or SO$_2$($C_{1-6}$alkyl)$R^9$;
Het is a heteroaryl ring chosen from pyridine, pyrimidine, pyrazine, pyridazine or triazine and optionally substituted by halogen, amino, hydroxy, cyano, nitro, carboxy, CONR$^{12}$R$^{13}$, SO$_2$NR$^{12}$R$^{13}$, SO$_2$R$^{12}$, trifluoromethyl, NHSO$_2$R$^{12}$, NHCOR$^{12}$, $C_{1-6}$alkyl, $C_{1-6}$alkoxy, SR$^{12}$ or NR$^{10}$R$^{11}$;
$R^3$ is independently hydrogen, $C_{1-6}$ alkyl or $C_{3-6}$cycloalkyl;
$R^4$ is independently hydrogen, $C_{1-8}$alkyl, $C_{3-8}$cycloalkyl, aryl$C_{1-5}$alkyl or heteroaryl$C_{1-5}$alkyl, the latter three groups being optionally substituted by one or more halogen, amino, hydroxy, $C_{1-6}$alkyl, $C_{1-6}$ alkoxy, SR$^{12}$ or NR$^{10}$R$^{11}$;
$R^5$ is independently hydrogen, $C_{1-6}$alkyl or $C_{3-6}$cycloalkyl;
$R^6$ is independently hydrogen, $C_{1-6}$alkyl or $C_{3-6}$cycloalkyl;
$R^7$ is independently hydrogen, $C_{1-6}$alkyl or $C_{3-6}$cycloalkyl;
$R^8$ is independently hydrogen, aryl, heteroaryl or $C_{1-6}$alkyl optionally substituted with one or more aryl, heteroaryl, halogen, amino, hydroxy, carboxy, CONR$^{12}$R$^{13}$, SO$_2$NR$^{12}$R$^{13}$, SO$_2$R$^{12}$, NHSO$_2$R$^{12}$, NHCOR$^{12}$, $C_{1-6}$alkyl, $C_{3-6}$cycloalkyl, $C_{1-6}$ alkoxy, SR$^{12}$ or NR$^{10}$R$^{11}$;
$R^9$ is aryl or heteroaryl;
$R^{10}$ and $R^{11}$ are independently hydrogen, $C_{1-6}$alkyl or together with the nitrogen atom to which they are attached form a 5- or 6-membered saturated ring optionally containing a further O, S or NR$^1$ group; and
$R^{12}$ and $R^{13}$ are independently hydrogen or $C_{1-6}$alkyl;
or a pharmaceutically acceptable salt thereof.

2. A compound according to claim 1 in which $R^1$ is hydrogen or $C_{1-6}$alkyl and $R^2$ is CH$_2$R$^9$ or CH$_2$CH$_2$R$^9$ where $R^9$ is phenyl or a 5- or 6-membered aromatic ring containing one or two heteroatoms and optionally substituted by $C_{1-6}$alkyl.

3. A compound according to claim 1 in which $R^3$ is hydrogen.

4. A compound according to claim 1 in which $R^4$ is hydrogen.

5. A compound according to claim 1 in which $R^5$ is hydrogen.

6. A compound of formula (I) selected from:
N-[2-(Benzylamino)pyrimidin-4-yl]-N-(cyanomethyl)-L-phenylalaninamide,
N-{2-[Benzyl(methyl)amino]pyrimidin-4-yl}-N-(cyanomethyl)-L-phenylalaninamide,
N~2~-[2-(Benzylamino)pyrimidin-4-yl]-N~1~-(cyanomethyl)-3-cyclohexyl-L-alaninamide,
N~2~-{2-[Benzyl(methyl)amino]pyrimidin-4-yl}-N~1~-(cyanomethyl)-3-cyclohexyl-L-alaninamide,
N~1~-(Cyanomethyl)-N~2~-{2-[methyl(pyridin-3-ylmethyl)amino]pyrimidin-4-yl}-L-leucinamide,
N~2~-{2-[Benzyl(methyl)amino]pyrimidin-4-yl}-N~1~-(cyanomethyl)-L-leucinamide,
N~1~-(Cyanomethyl)-N~2~-{2-[methyl(thien-3-ylmethyl)amino]pyrimidin-4-yl}-L-leucinamide,
N~1~-(Cyanomethyl)-N~2~-{2-[methyl(2-pyridin-2-ylethyl)amino]pyrimidin-4-yl}-L-leucinamide,
N~1~-(Cyanomethyl)-N~2~-(2-{methyl[(3-methylisoxazol-5-yl)methyl]amino}pyrimidin-4-yl)-L-leucinamide,
and pharmaceutically acceptable salts thereof.

7. A pharmaceutical composition which comprises a compound as defined in claim 1 or a pharmaceutically acceptable salt thereof and a pharmaceutically acceptable diluent or carrier.

8. A compound according to claim 1 in which $R^4$ is phenyl$C_{1-5}$alkyl being optionally substituted by one or more halogen, amino, hydroxy, $C_{1-6}$alkyl, $C_{1-6}$alkoxy, SR$^{12}$ or NR$^{10}$R$^{11}$.

9. A compound according to claim 1 in which $R^5$ is $C_{1-6}$alkyl.

10. A compound according to claim 1 in which $R^5$ is isobutyl.

11. A compound according to claim 1 in which $R^6$ is hydrogen.

12. A compound according to claim 1 in which $R^7$ and $R^8$ are both hydrogen.

13. A compound according to claim 1 in which $R^9$ is phenyl, pyridyl or oxazole substituted by methyl.

14. A pharmaceutical composition which comprises a compound according to claim 13 or a pharmaceutically acceptable salt thereof and a pharmaceutically acceptable diluent or carrier.

15. A compound according to claim 1 in which Het is a pyrimidine ring.

* * * * *

UNITED STATES PATENT AND TRADEMARK OFFICE
CERTIFICATE OF CORRECTION

PATENT NO.        : 7,605,159 B2
APPLICATION NO.   : 10/538452
DATED             : October 20, 2009
INVENTOR(S)       : Judith McInally et al.

It is certified that error appears in the above-identified patent and that said Letters Patent is hereby corrected as shown below:

Column 15
Line 55, delete "$C_{1-6\ l\ alkoxy,\ SR}{}^{12}$" -- insert -- $C_{1-6}$alkoxy, $SR^{12}$ --

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,605,159 B2 | Page 1 of 1 |
| APPLICATION NO. | : 10/538452 | |
| DATED | : October 20, 2009 | |
| INVENTOR(S) | : McInally et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 434 days.

Delete the phrase "by 434 days" and insert -- by 754 days --

Signed and Sealed this

Twentieth Day of April, 2010

David J. Kappos
*Director of the United States Patent and Trademark Office*